United States Patent [19]

Boretos

[11] 4,403,985

[45] Sep. 13, 1983

[54] JET CONTROLLED CATHETER

[75] Inventor: John W. Boretos, Rockville, Md.

[73] Assignee: The United States of America as represented by the Department of Health and Human Services, Washington, D.C.

[21] Appl. No.: 262,806

[22] Filed: May 12, 1981

[51] Int. Cl.$^3$ ............................................. A61M 25/00
[52] U.S. Cl. ........................................ 604/53; 604/95
[58] Field of Search ................... 128/4, 6, 348–350 R, 128/276, 239, 657, 772; 604/95, 53

[56] References Cited

U.S. PATENT DOCUMENTS

| 2,356,659 | 8/1944 | Aguiar | 128/276 |
| 2,855,934 | 10/1958 | Daughaday | 128/349 R |
| 3,071,137 | 1/1963 | Niebel et al. | 128/276 |
| 3,605,725 | 9/1971 | Bentov | 128/657 |
| 3,665,928 | 5/1972 | Del Guercio | 128/350 R |
| 3,773,034 | 11/1973 | Burns et al. | 128/348 X |

Primary Examiner—Dalton L. Truluck
Attorney, Agent, or Firm—Holman & Stern

[57] ABSTRACT

The leading end of a catheter tube is directionally controlled by reactive forces imparted to the tube by pressurized control fluid issued from selected control ports defined through the tube proximate its forward end. The reactive forces can be used to bend, turn, propel and otherwise maneuver the advancing catheter. A circumferentially pleated section of the tube may be provided to facilitate bending. A flexible and annular flow baffle may be disposed in the control port outflow path to minimize control flow impact on the vessel wall and/or to affect thrust direction.

14 Claims, 4 Drawing Figures

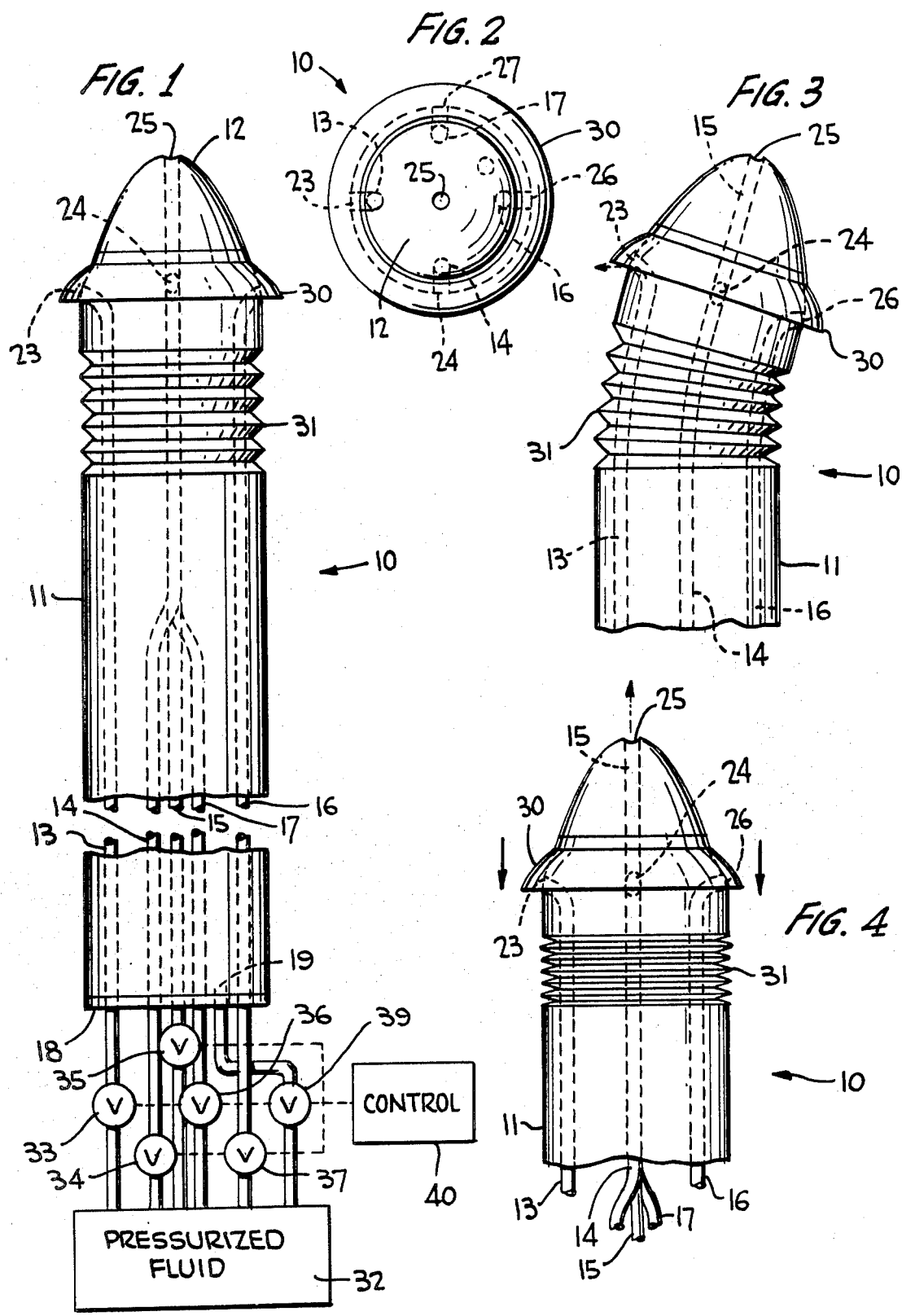

JET CONTROLLED CATHETER

TECHNICAL FIELD

The present invention relates generally to catheters and, more particularly, to controlling the movement of the catheters in acutely branching vessels without the need for stiff and abrasive guide wires or other cumbersome mechanical means.

BACKGROUND OF THE INVENTION

Catheters are widely used by the clinical radiologist and the surgeon. In addition, catheters find application in diagnosing and treating many ailments. They are used in virtually all passageways of the body, from blood vessels and urinary tracts to nasal and throat openings. Catheters function to augment flow of blood, air, urine, or as a means of treatment through drug delivery and removal of plaque and clots.

One of the great difficulties in utilizing catheters in the vascular system relates to the control of movement of the catheter through the variously branching vessels. A common form of vascular system catheter is described in U.S. Pat. No. 3,687,142 and contains a balloon-like member which assists in "floating" the catheter along with the flow of blood. However, navigating the balloon-like member selectively into and through tortuous side vessels is quite difficult and, in many cases, impossible. Toposcopic catheter designs permit movement of the catheter through vessels but have no provision for guiding and are therefore largely limited to non-bifurcated or non-branching vessels.

SUMMARY OF THE INVENTION

It is an object of the present invention to provide a novel means and method for controlling the movement of a catheter into and through tortuous passages such as are found in the vascular system. It is a further object of the present invention to provide a readily controlled guidance arrangement to permit a catheter to traverse a selected tortuous path in the vascular system without the need for stiff and abrasive guide wires or other cumbersome mechanical means.

In accordance with the present invention, the leading end of a catheter is caused to bend, turn, be propelled, or otherwise be maneuvering by issuing jets of control fluid from the catheter to impart jet reactive forces thereto. The jets may be constant streams or pulsatile and are issued from selected control ports disposed at circumferentially spaced locations proximate the forward end of the catheter tube. Reverse movement of the catheter can be effected by issuing fluid from a control portion disposed at the forward tip of the catheter tube. The tube is preferably circumferentially pleated at a location just rearward of the circumferentially spaced control ports in order to facilitate bending of the tube upon application of a reactive jet force thereto. A flexible annular flow baffle may be secured concentrically about the catheter tube, forward of the circumferentially spaced control ports, so that the control flow issued from the control ports strikes the baffle and does not impact with significant force against the vessel walls. By selectively controlling flow from various control ports, the clinical radiologist or surgeon can guide the catheter tip into difficult to reach areas with a less traumatic means of maneuvering the catheter than has previously been possible.

BRIEF DESCRIPTION OF THE DRAWINGS

The above and still further objects, features, and advantages of the present invention will become apparent upon consideration of the following detailed description of one specific embodiment thereof, especially when taken in conjunction with the accompanying drawings, wherein:

FIG. 1 is an exploded, partially diagrammatic plan view of a catheter constructed in accordance with the present invention;

FIG. 2 is a plan view of the forward end of the catheter of FIG. 1;

FIG. 3 is a side view in plan of the forward end of the catheter of FIG. 1 in a bent condition during one mode of operation; and FIG. 4 is a side view in plan of the forward end of the catheter of FIG. 1 in a retracted position as occurs during another mode of operation.

DESCRIPTION OF THE PREFERRED EMBODIMENTS

Referring specifically to FIGS. 1 and 2 of the accompanying drawings, a jet controlled catheter of the present invention is generally designated by the reference numeral 10. The catheter 10 is in the form of an elongated tube 11 made from any soft thermoplastic or elastomeric material which can be made in the form of a tube. Sample materials are polyurethanes, copolyester polymers, silicone rubber, polyethylene, polyvinylchloride, etc. Tube 11 is a thin-walled tube having a convex tapered forward end 12. A plurality of flow passages 13 through 17 extend longitudinally through tube 11 from its rearward end 18 to proximate forward end 12. The number of such flow passages to be employed depends upon the particular design and operational requirements for the catheter. The exemplary embodiment illustrated in FIGS. 1 and 2 shows five (5) such passages. Passages 13, 14, 16 and 17 terminate in respective control ports 23, 24, 26 and 27 which are circumferentially spaced from one another at a location slightly rearward of the forward end 12 of the tube. A further control port 25 is defined at the extreme tip of forward end 12 and serves at a termination for flow passage 15. A further flow passage 19 may be provided and positioned to deliver pressurized fluid into the interior of the tube 11 at its rearward end 18.

An annular baffle member 30 is made of flexible material, preferably of the same type of material as tube 11, and includes a radially inward edge which is secured to tube 11 at forward end 12 at a location longitudinally intermediate control port 25 and control ports 23, 24, 26 and 27. The radially outward end of baffle member 30 extends radially outward and longitudinally rearward to overlie control ports 23, 24, 26 and 27 without impeding outflow from these ports.

A bellowed or pleated section 31 of tube 11 is provided slightly rearward of control ports 23, 24, 26 and 27. This bellowed section permits the forward end of tube 11 to be readily flexed off-axis, as illustrated in FIG. 3, or longitudinally expanded or compressed, as illustrated in FIG. 4. Bellowed or pleated section 31 is formed by providing a plurality of annular folds in the tube.

The rearward end 18 receives the flow passages 13, 14, 15, 16, 17 and 19 which are connected to a source of pressurized fluid 32. Respective valves 33, 34, 35, 36, 37, and 39 are disposed in each of the flow passages 13, 14, 15, 16, 17 and 19 to permit individual control of pressurized fluid flow through the flow passages. Alternatively, a common control mechanism 40 may be employed to permit synchronized operation of the individual valves.

In a typical operation of catheter 10, tube 11 is initially coiled or otherwise retracted within a larger diameter catheter which is introduced into a large blood vessel such as the femoral artery. When the large diameter catheter is extended through the vascular system to the limit its diameter will allow, the catheter 10 may be extended, or may swim, through the larger diameter catheter by introducing pressurized fluid into the interior of tube 11 through actuation of valve 39. In other words, the small-diameter flaccid tube 11 is propelled through the larger diameter catheter to the forward end of that catheter by means of the pressurized fluid introduced from source 32 and passage 19. Upon reaching the end of the larger diameter catheter, tube 11 projects forwardly outward therefrom into the smaller vessels in the vascular system. Continued pressurization of the interior of tube 11 via flow passage 19 results in continued forward movement of the tube. In order to achieve directional control, pressurized fluid from source 32 is directed by means of the appropriate valve to the appropriate flow passage. For example, as illustrated in FIG. 3, if it is desired to bend or flex the tube 11 to the right, as illustrated in FIG. 3, control fluid is introduced into passage 13 by actuating valve 33 so that the fluid is caused to flow outward from control port 23. The control fluid jet, upon issuing from control port 23, produces a reactive force on the forward end of the catheter which results in flexure of the bellowed section 31 and a bending of the tube at that point. By admitting pressurized control fluid to any one or more of the flow passages 13, 14, 16 and 17, the direction of bending can be accurately controlled, it being noted that two or more control jets produce a reactive force which is equal and opposite to their resultant vector. If it is desired to slightly retract the forward end 12 of tube 11, control fluid is introduced to passage 15 via valve 35 so as to be issued from the forward end at control port 25. The reactive force on the tube, opposite to that of the issue jet, causes the bellowed section 31 to retract.

Baffle member 30 is provided to prevent the outflowing jet of control fluid from impinging with too much force on the relatively thin vessel walls.

The control fluid employed is an isotonic fluid, such as Dextran or other such sterile fluid, which is compatible with the blood in the vascular system. Alternatively, a radiological dye fluid may be employed.

It should be understood that it is possible to dispense with a number of the control ports and still obtain accurate control of the motion of tube 11. For example, the circumferentially spaced control ports 23, 24, 26 and 27 can be reduced in number to three (3) while still maintaining the capability of flexing tube 11 in any direction. Likewise, control port 25 can be dispensed with and other means for retracting the tube can be employed. It should also be noted that forward motion can be imparted by the use of the circumferentially spaced control ports if they are baffled so that the exiting flow is directed into an extreme reverse angle whereby to provide forward thrust.

The flow passages 13, 14, 15, 16 and 17 are shown as individual passages extending through the length of tube 11. It may be preferred to have these passages formed as channels in the wall of the tube 11 rather than as individual passages spaced from that wall. Such an embodiment is certainly within the contemplation and scope of the present invention. In an actual embodiment which has been tested, tubes as small as 0.034 inches in outside diameter have been successively manuvered into extremely angled branches of the vascular system by surging control fluid through one or more of the control ports. The force generated by the jet reaction permitted movement of the catheter sideways, forward and in a reverse direction. I have found that a 10 cc syringe can deploy three (3) feet of tube 11 through a larger diameter catheter with only about 2 cc of control fluid used to pressurize passage 19. Effective motion control is provided through a tube of approximately five (5) feet in length with pressures as low as 1 psi or less of control fluid. The flexible baffle member 30 protects even the most fragile of blood vessel walls from the force of the jet.

While I have described and illustrated a specific embodiment of my invention, it will be clear that variations of the details of construction which are specifically illustrated and described may be resorted to without departing from the true spirit and scope of the invention as defined in the appended claims.

I claim:

1. An improved vascular catheter arrangement for use in traversing a network of tortuous blood vessel passages, comprising:
    an elongated flexible catheter tube for traversing said blood vessel passages and having a forward end and a rearward end, said tube also having a circumferential periphery with a plurality of control ports defined therethrough at predetermined angularly spaced locations proximate said forward end; and
    control means for controllably bending said tube transversely of the length of the tube, within said blood vessel passage network, by selectively delivering pressurized fluid from said rearward end for issuance through selected control ports to impart transversely directed reactive thrust forces on said tube proximate said forward end.

2. The catheter according to claim 1 wherein said control means includes a plurality of individual flow passages within said tube, each passage connected to selectively and individually conduct fluid from said rearward end of said tube to a respective control port.

3. The catheter according to claim 2 wherein said individual control passages are individual flow tubes disposed within said catheter tube.

4. The catheter according to claim 2 wherein said flow passages are individual flow channels defined in the interior wall of said catheter tube.

5. The catheter according to claim 1 wherein at least one control port is located at the extreme forward end of said catheter tube.

6. An improved catheter arrangement comprising:
    an elongated flexible catheter tube having a forward end and a rearward end, said tube having a plurality of control ports defined therethrough at predetermined locations proximate said forward end;
    control means for positioning said tube in situ by selectively delivering pressurized fluid from said rearward end for issuance through selected control ports to impart reactive thrust forces on said tube proximate said forward end;
    wherein said control ports are positioned at angularly spaced locations in the circumferential periphery of said catheter tube; and flow baffle means in the form of a flexible flap having radially inner and outer edges, the inner edge of said flap being secured to said catheter tube at a location between said control ports and said forward end of said catheter tube, said flap having a sufficiently large radial dimension so as to extend into the path of fluid being issued from said control ports.

7. The catheter according to claim 6, wherein said catheter tube has a circumferentially pleated section near its forward end rearward of said control ports, to facilitate bending of said catheter tube.

8. The catheter according to claim 7, wherein said control means comprises means for individually controlling flow of pressurized fluid to each of said control ports.

9. The catheter according to claims 1 or 2, wherein said catheter tube has a circumferentially pleated section near its forward end rearward of said control ports, to facilitate bending of said catheter tube.

10. The catheter according to claim 9 wherein said control means comprises means for individually controlling flow of pressurized fluid to each of said control ports.

11. The catheter according to claim 1 wherein said control means comprises means for delivering said pressurized fluid to said control ports as discrete fluid pulses.

12. A method of controlling movement of a catheter tube through blood vessels comprising the step of selectively issuing pressurized fluid from different locations of said catheter tube to externally of said catheter tube so as to impart selective transversely-directed reactive forces to said catheter tube.

13. The method according to claim 12 wherein said step of selectively issuing includes issuing the pressurized fluid in selected radially outward directions with respect to said catheter tube, to cause the tube to bend away from the flow direction of the issued fluid.

14. The method according to claim 12 wherein the step of issuing includes issuing the pressurized fluid in at least two selected radially outward directions from said catheter tube to cause the tube to bend in a direction radially opposite the vectorial sum of the at least two issued fluid flows.

* * * * *